United States Patent
Chen et al.

(10) Patent No.: US 10,458,928 B2
(45) Date of Patent: Oct. 29, 2019

(54) COLLIMATING DEVICE AND RAY INSPECTION DEVICE

(71) Applicants: Nuctech Company Limited, Beijing (CN); Nuctech Jiangsu Company Limited, Jiangsu (CN)

(72) Inventors: Zhiqiang Chen, Beijing (CN); Wanlong Wu, Beijing (CN); Ziran Zhao, Beijing (CN); Guangwei Ding, Beijing (CN); Ming Ruan, Beijing (CN); Xilei Luo, Beijing (CN)

(73) Assignees: Nuctech Company Limited, Beijing (CN); Nuctech Jiangsu Company Limited, Jiangsu (CN)

( * ) Notice: Subject to any disclaimer, the term of this patent is extended or adjusted under 35 U.S.C. 154(b) by 0 days.

(21) Appl. No.: 15/578,131

(22) PCT Filed: May 19, 2016

(86) PCT No.: PCT/CN2016/082600
§ 371 (c)(1),
(2) Date: Nov. 29, 2017

(87) PCT Pub. No.: WO2017/075963
PCT Pub. Date: May 11, 2017

(65) Prior Publication Data
US 2018/0292333 A1 Oct. 11, 2018

(30) Foreign Application Priority Data
Nov. 6, 2015 (CN) .......................... 2015 1 0751623

(51) Int. Cl.
*G21K 1/02* (2006.01)
*G01N 23/223* (2006.01)
(Continued)

(52) U.S. Cl.
CPC ............ *G01N 23/083* (2013.01); *G01N 23/02* (2013.01); *G21K 1/025* (2013.01); *G01N 2223/316* (2013.01)

(58) Field of Classification Search
CPC ....... G01N 2223/316; G01N 2223/313; G01N 23/083
See application file for complete search history.

(56) References Cited

U.S. PATENT DOCUMENTS

| 2,831,977 A | 4/1958 | Henke |
| 3,327,114 A | 6/1967 | Diorio et al. |

(Continued)

FOREIGN PATENT DOCUMENTS

| CN | 1936538 A | 3/2007 |
| CN | 101114534 A | 1/2008 |

(Continued)

OTHER PUBLICATIONS

"International Search Report and Written Opinion", w/English Translation, (dated Aug. 22, 2016), 12 pgs.

(Continued)

*Primary Examiner* — Don K Wong
(74) *Attorney, Agent, or Firm* — Schwegman Lundberg & Woessner, P.A.

(57) ABSTRACT

Embodiments of the present disclosure provide a collimating device and a ray inspection device. The collimating device comprises: a beam guiding cylinder, a first collimator mounted at an inlet end of the beam guiding cylinder; a second collimator mounted an outlet end of the beam guiding cylinder; a beam guiding cylinder adjusting device disposed adjacent to the inlet of the beam guiding cylinder to adjust a direction of the beam guiding cylinder such that the first collimator is aligned with the first direction. The outlet end of the beam guiding cylinder is fixed to the frame and the second collimator is aligned with an object to be (Continued)

irradiated by a radiation beam, and the beam guiding cylinder is configured to have flexibility to allow the adjusting device to adjust a direction towards which the inlet end of the beam guiding cylinder is directed, in a direction transverse to the first direction.

13 Claims, 2 Drawing Sheets

(51) Int. Cl.
    *G01N 23/083*     (2018.01)
    *G01N 23/02*     (2006.01)

(56) References Cited

U.S. PATENT DOCUMENTS

| | | |
|---|---|---|
| 2005/0148841 A1 | 7/2005 | Kamath et al. |
| 2011/0235778 A1 | 9/2011 | Toh et al. |
| 2011/0255662 A1* | 10/2011 | Shannon, Jr. ........ G01N 23/223 378/44 |

FOREIGN PATENT DOCUMENTS

| | | |
|---|---|---|
| CN | 201142237 Y | 10/2008 |
| CN | 101482653 A | 7/2009 |
| CN | 201886195 U | 6/2011 |
| CN | 103823275 A | 5/2014 |
| CN | 105223211 A | 1/2016 |
| KR | 101242731 B1 | 3/2013 |

OTHER PUBLICATIONS

"European Application Serial No. 16861236.4, European Search Report dated Jun. 5, 2019", (dated Jun. 5, 2019), 9 pgs.

* cited by examiner

COLLIMATING DEVICE AND RAY INSPECTION DEVICE

CROSS-REFERENCE TO RELATED APPLICATIONS

This application is a U.S. National Stage Filing under 35 U.S.C. 371 from International Application No. PCT/CN2016/082600, filed on May 19, 2016, and published as WO2017/075963 on May 11, 2017, which application claims the benefit of Chinese Patent Application No. 201510751623.7, entitled of "collimating device and ray inspection device", and filed on Nov. 6, 2015 in the State Intellectual Property Office of China, the disclosures of each of which are incorporated herein by reference.

BACKGROUND

1. Technical Field

Embodiments of the present disclosure relate to field of detection by a ray, and particularly to a collimating device and a ray inspection device.

2. Description of the Related Art

A ray inspection device in prior art includes a collimating device, which generally includes a plurality of collimators. In order to align these collimators, in a ray beam collimating method, generally a second collimator and a detector collimator are firstly collimated by using a laser pen, positions of them are fixed, and then a first collimator is mounted and the second collimator, the first collimator and the detector collimator aligned with one another by using the laser pen. Finally, an X-ray machine is mounted and is adjusted to align a target point of the X-ray machine, the first collimator, the second collimator and the detector collimator with one another by using radiation dose. Alternatively, alignment adjustment may be performed from the X-ray source. However, this alignment adjustment in stepwise manner is troublesome and consumes time and labor when performed. Further, adjustment and alignment need to be performed again after one detection process due to vibration and movement during the detection process. Thus, collimation adjustment of the device in prior art will consume a mass of time and reduces a detection efficiency.

SUMMARY

Embodiments of the present disclosure provide a collimating device and a ray inspection device having a simplified structure, easy to achieve alignment and having a high efficiency.

In an aspect, there is provided a collimating device, mounted to a frame and configured to collimate a radiation beam from a source, the collimating device comprising:

a beam guiding cylinder extended along a first direction such that the radiation beam enters the beam guiding cylinder from an inlet thereof in the first direction, passes along the beam guiding cylinder and is emitted out of an outlet of the beam guiding cylinder;

a first collimator mounted at an inlet end of the beam guiding cylinder;

a second collimator mounted at an outlet end of the beam guiding cylinder; and a beam guiding cylinder adjusting device disposed adjacent to the inlet of the beam guiding cylinder to adjust a direction of the beam guiding cylinder such that the first collimator is aligned with the first direction;

wherein the outlet end of the beam guiding cylinder is fixed to the frame and the second collimator is aligned with an object to be irradiated by the radiation beam, and the beam guiding cylinder is configured to have flexibility to allow the beam guiding cylinder adjusting device to adjust a direction towards which the inlet end of the beam guiding cylinder is directed, in a direction transverse to the first direction.

In another aspect, there is provided a ray inspection device comprising a frame, wherein the ray inspection device further comprises the components that are mounted to the frame: a ray source configured to generate ray; an inspection region where an object to be inspected is placed or is passed; a detecting device configured to detect ray signal that has penetrated the object to be inspected; and the collimating device as described above.

DETAILED DESCRIPTION OF THE EMBODIMENTS

Figure 1:
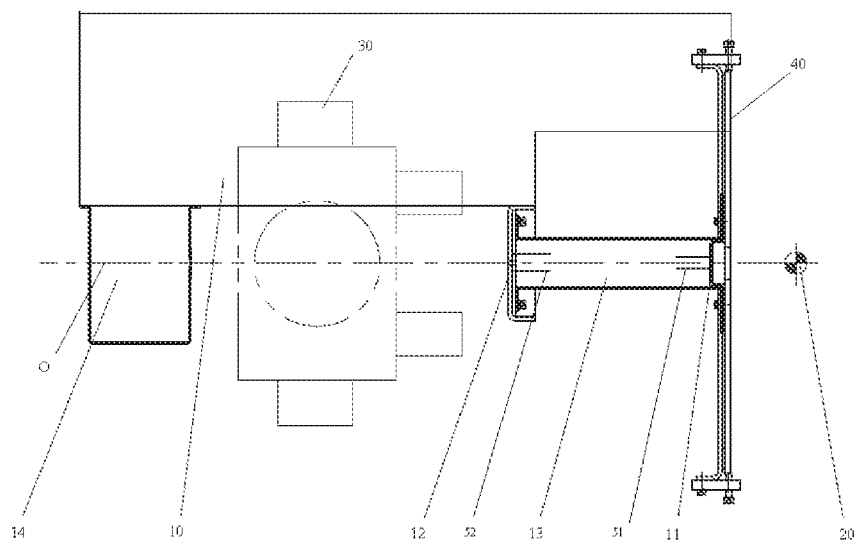
FIG. 1 illustrates a ray inspection device according to an embodiment of the present disclosure.

A further description of embodiments of the present disclosure will be made in detail and the embodiments are illustrated in the accompanying drawings. In the drawings, similar component is represented by the same reference number. The following embodiments will be described with reference to the accompanying drawings.

According to an embodiment of the present disclosure, there is provided a collimating device mounted to a frame 10 and configured to collimate a radiation beam from a source. As shown in FIG. 1, the collimating device includes: a beam guiding cylinder 13 extended along a first direction such that the radiation beam enters the beam guiding cylinder 13 from an inlet thereof in the first direction as shown by the arrow, passes along the beam guiding cylinder 13 and is emitted out of an outlet of the beam guiding cylinder 13; a first collimator 11 mounted at an inlet end of the beam guiding cylinder 13; a second collimator 12 mounted an outlet end of the beam guiding cylinder 13; a beam guiding cylinder adjusting device 40 disposed adjacent to the inlet to adjust the beam guiding cylinder 13 such that the first collimator 11 is aligned with the first direction. In the embodiment, the outlet end of the beam guiding cylinder 13 is fixed to the frame 10 and the second collimator 12 is aligned with an object to be irradiated by the radiation beam, for example, a detector configured to receive the radiation beam. The beam guiding cylinder 13 may be further configured to have flexibility to allow it to deform such that the adjusting device can adjust a direction towards winch the inlet end of the beam guiding cylinder 13 is directed, in a direction transverse to the first direction.

In the embodiment, the frame 10 may be made of metal material, plastic material or any material, and preferably, material that can absorb vibration such that influence of external vibration on the frame 10 is as small as possible. In the embodiment, the first collimator 11 and the second collimator 12 are made of metal. The first collimator 11 and the second collimator 12 each include a narrow slit to allow a ray to pass through the collimator such that the ray is collimated. It is understood that a collimator in prior art may be used herein. In the embodiment, the beam guiding cylinder 13 is made of a flexible material, such as a metal material. In the embodiment, the ray is transmitted in the beam guiding cylinder 13 and will not be transmitted to an outside of the beam guiding cylinder 13. Any suitable material may be used to form the beam guiding cylinder 13.

In the embodiment, the beam guiding cylinder adjusting device 40 includes a retractable adjusting rod 42 configured to extend and retractably move in a direction transverse to the first direction so as to adjust the direction towards which the inlet end of the beam guiding cylinder 13 is directed. In an embodiment, the retractable adjusting rod 42 may comprise two retractable adjusting rods. For example, as shown in FIG. 1, two retractable adjusting rods 42 are respectively in contact with the inlet end of the beam guiding cylinder 13 such that protrusion and retraction movements, in an up-down direction, of the two retractable adjusting rods which cooperate with each other can cause the inlet end of the beam guiding cylinder 13 to move in the up-down direction.

In the embodiment, the beam guiding cylinder adjusting device 40 may further include a beam guiding cylinder adjusting screw 43 configured to move the retractable adjusting rod 42 in the direction transverse to the first direction by being screwed. A movement of the retractable adjusting rod 42 in the up-down direction may be achieved by screwing movement of the beam guiding cylinder adjusting screw 43.

In the embodiment, the beam guiding cylinder adjusting device 40 may further include a fixing plate 41 configured to fix the inlet end of the beam guiding cylinder 13 and extend in a plane transverse to the first direction. The plane transverse to the first direction may be understood as a plane perpendicular to the first direction. After completing adjustment of the direction towards which the inlet end of the beam guiding cylinder 13 is directed by the retractable adjusting rod 42, the inlet end of the beam guiding cylinder 13 is fixed by the fixing plate 41 so as to perform a next operation, such as irradiation. The fixing plate 41 may be a strip plate, or may be a rectangle plate, or may be a plate in other shape. Both ends of the fixing plate are respectively fixed to the frame 10 such that the fixing plate 41 cannot be moved. In order to fix the inlet end of the beam guiding cylinder 13, the inlet end of the beam guiding cylinder 13 may be detachably fixed to the fixing plate 41.

In the embodiment, the beam guiding cylinder adjusting device 40 may further include: a flange plate 46 coupled to the inlet end of the beam guiding cylinder 13, the flange plate 46 including a portion extending along a plane where the fixing plate 41 is located and a portion coupled to the inlet end of the beam guiding cylinder 13; and, a fastening screw 45 that is mounted to a threaded hole in the flange plate 46. The fastening screw 45 contacts and presses the fixing plate 41 by being screwed into the threaded hole, so as to fix the flange plate 46 and the inlet end of the beam guiding cylinder 13 coupled to the flange plate 46 to a position of the fixing plate 41 by means of a friction three between the fastening screw 45 and the fixing plate 41, thereby fixing the direction towards which the inlet end of the beam guiding cylinder 13 is directed. When releasing the fastening screw 45, the inlet end of the beam guiding cylinder 13 can be moved in the plane transverse to the first direction, in an up-down direction.

In an embodiment of the present disclosure, the retractable adjusting rod 42 may comprise four retractable adjusting rods and is configured to retractably move in four directions, i.e., upward, downward, leftward and rightward directions, in the transverse plane perpendicular to the first direction, so as to adjust the direction towards which the inlet end of the beam guiding cylinder is directed. In order to be able to adjust the direction towards which the inlet end of the beam guiding cylinder 13 is directed in upward and downward directions, and forward and backward directions perpendicular to the plane of the paper, four retractable adjusting rods 42 may be provided. FIG. 1 shows two retractable adjusting rods 42 that cooperate in the upward and downward directions. The other two retractable adjusting rods (not shown) are disposed in a direction perpendicular to the plane of the paper to cooperate with each other. In this embodiment, the configuration of the fixing plate 41 and the fastening screw 45 of the above embodiment may be used without change. In the embodiment, the direction towards which the inlet end of the beam guiding cylinder 13 is directed may be adjusted in any direction in the plane transverse to the first direction (i.e., a plane perpendicular to the plane of the paper). In the other words, the direction towards which the inlet end of the beam guiding cylinder 13 is directed may be adjusted upwards, downwards, leftwards and rightwards in a direction transverse to the first direction or in the plane transverse to the first direction. Herein the direction transverse to the first direction includes any directions in the plane transverse to the first direction. According to the embodiment, a collimation adjustment of the collimating device can be achieved by merely adjusting the first collimator, which is convenient for practical use and can save much time for collimation adjustment.

Figure 2:
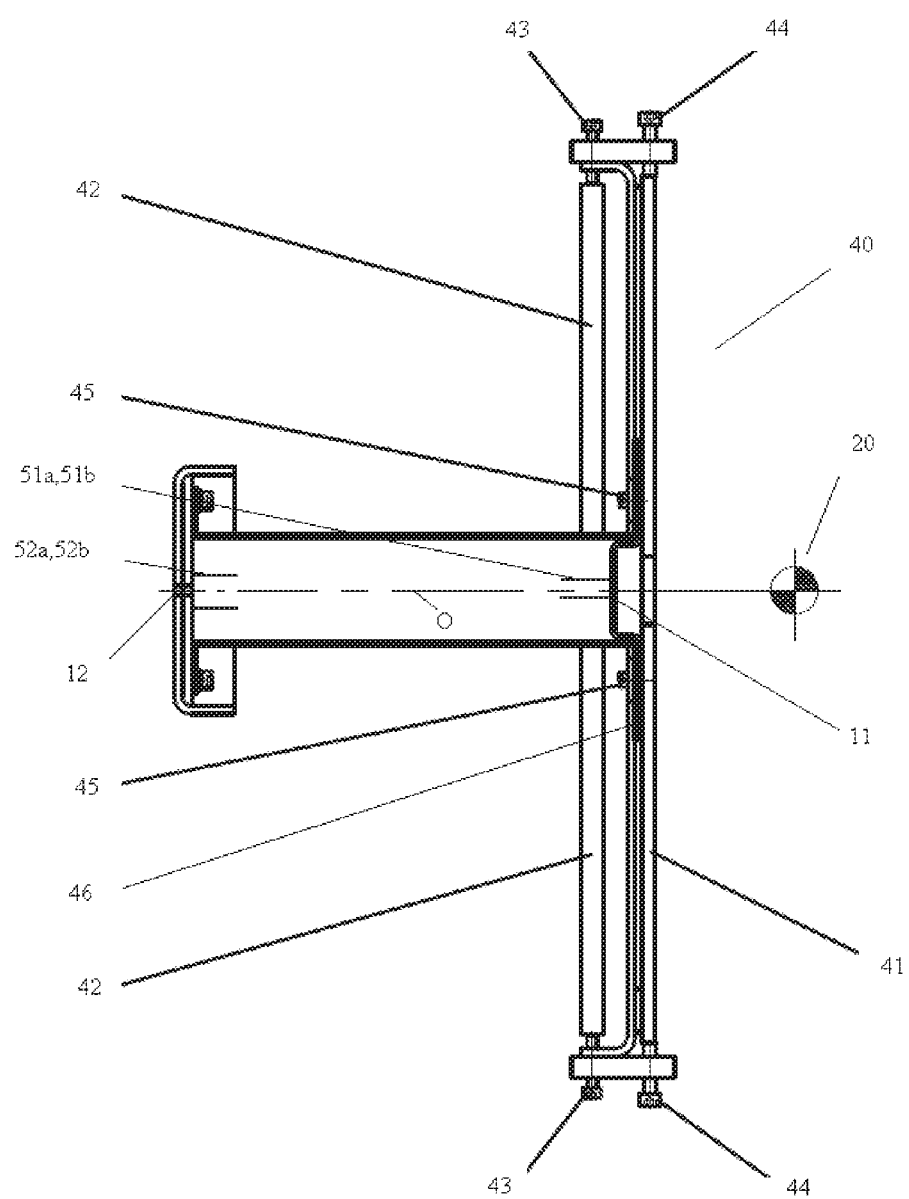
FIG. 2 illustrates a collimating device according to an embodiment of the present disclosure.

In an embodiment of the present disclosure, the beam guiding cylinder further includes a collimation enhancing piece 51, 52 extending in the first direction, for example, extending along a central axis O as shown in FIGS. 1 and 2. The collimation enhancing piece may comprise two collimation enhancing pieces. For example, a first collimation enhancing piece 51 is provided at the first collimator 11 and a second collimation enhancing piece 52 is provided at the second collimator 12. The first and second collimation enhancing pieces 51, 52 are sized such that most of scattering rays passing through the first collimator 11 and/or the second collimator 12 are blocked by the collimation enhancing pieces 51, 52. In an embodiment, the collimation enhancing pieces 51, 52 are made of a second material that can absorb a ray, or, sides of the collimation enhancing pieces 51, 52 facing the central axis of the beam guiding cylinder are coated with the second material that can absorb the ray so as to absorb a scattering ray passing through the first collimator 11 and/or the second collimator 12. The collimation enhancing pieces 51, 52 each include a first portion coupled to the first collimator and/or the second collimator and a second portion extending parallel to the central axis O of the beam guiding cylinder. The collimation enhancing pieces 51, 52 include first baffle plates 51a, 52a and second baffle plates 51b, 52b, respectively, and the first baffle plates 51a, 52a and the second baffle plates 51b, 52b are positioned symmetrically with respect to the central axis O of the beam guiding cylinder, respectively.

In an embodiment, the first collimation enhancing piece 51 or the second collimation enhancing piece 52 may be constituted by a baffle plate that is located at a side of the central axis of the beam guiding cylinder.

Embodiments of the present disclosure further provide a ray inspection device comprising a frame 10. The ray inspection device further includes other components or devices that are mounted to the frame 10. The frame 10 is advantageously made of a material that can absorb vibration so that external vibration affects collimation of the collimating device as little as possible. The frame 10 may also be made of other materials. The frame 10 itself may be provided with a vibration absorbing device, such as a vibration absorbing air base, or the like, so as to reduce interference of external vibration with alignment.

In an embodiment of the present disclosure, the ray inspection device may further include the following components that are mounted to the frame 10: a ray source configured to generate a ray; an inspection region where an object to be inspected is placed or is passed; a detecting device configured to detect a ray signal that has penetrated the object to be inspected; and the collimating device as described above.

In an embodiment of the present disclosure, the ray source may be an X-ray source. The inspection region may be in the form of a passage, or may be provided with a track, such as an active belt conveyor or the like, or may be in other form. When the object to be inspected is passing within the inspection region, a ray emitted by the ray source penetrates the object to be inspected, such that the object to be inspected can be viewed by detecting penetrated a transmitted ray. The inspection region is located at a distance from the outlet end of the collimating device. The specific configuration of the detecting region may be set according to a structure of the frame 10 or a volume of the object to he inspected.

In an embodiment of the present disclosure, the detecting device may include a detector configured to detect the ray that has penetrated the object to be inspected. The detector may be a single detector, or may include a plurality of detectors, such as a row of detector or an array of detectors consisting of a plurality of rows of detectors. The inspection device may further include a detector collimator 14 configured to allow the ray that has penetrated the object to be inspected to enter the detector. In the embodiment, the detector collimator 14 is aligned with the second collimator 12 of the collimating device and is fixed to the frame 10.

In the embodiment, the detector collimator 14 and the second collimator 12 of the collimating device are both fixed to the frame 10 and are aligned with each other. With this configuration, alignment between the second collimator 12 of the collimating device and the detector collimator 14 is fixed and does not need to be adjusted during subsequent inspection process, thereby simplifying the inspection process.

In the embodiment, the X-ray source of the ray inspection device, such as an X-ray machine, may be fixed to the fixing plate 41. In this instance, the entire ray inspection device is fixed to the frame 10, except that the inlet end of the beam guiding cylinder 13 is movable so as to be adjusted.

In the embodiment, the X-ray source, the inlet end of the first collimator 11 and the beam guiding cylinder adjusting device of the ray inspection device may be considered as a first part while the second collimator 12, the detecting device and the inspection region of the ray inspection device may be considered as a second part. According to the embodiment, before using the ray inspection device to detect an object to he inspected, a common light source is used to adjust the collimating device. For example, a lamp is provided and configured to allow light to enter the first collimator 11; then, the beam guiding cylinder adjusting device is adjusted to adjust a direction towards which the inlet end of the beam guiding cylinder 13 is directed, such that light penetrated passing through the first collimator 11 is aligned with the second collimator 12, and further aligned with the detector collimator 14. Subsequently, the X-ray source is activated to emit rays. With the configuration according to the embodiment, alignment of the ray inspection device may be achieved by aligning the first part of the ray inspection device by merely adjusting the inlet end of the beam guiding cylinder 13. Thus, the ray inspection device according to embodiments of the present disclosure may be operated in more simply way and in higher efficiency way.

The above embodiments are referred to explain the present disclosure and specifically illustrate and show the present disclosure. However, it will be understood by those skilled in the art that various changes and modifications may be made therein without departing from the spirit of the present disclosure, the scope of which is defined in the appended claims and their equivalents.

The invention claimed is:

1. A collimating device, mounted to a frame and configured to collimate a radiation beam from a source, the collimating device comprising:
   a beam guiding cylinder extended along a first direction such that the radiation beam enters the beam guiding cylinder from an inlet thereof in the first direction, passes along the beam guiding cylinder and is emitted out of an outlet of the beam guiding cylinder;
   a first collimator mounted at an inlet end of the beam guiding cylinder;
   a second collimator mounted at an outlet end of the beam guiding cylinder; and
   a beam guiding cylinder adjusting device disposed adjacent to the inlet of the beam guiding cylinder to adjust a direction of the beam guiding cylinder such that the first collimator is aligned with the first direction;
   wherein the outlet end of the beam guiding cylinder is fixed to the frame and the second collimator is aligned with an object to be irradiated by the radiation beam, and the beam guiding cylinder is configured to have flexibility to allow the beam guiding cylinder adjusting device to adjust a direction towards which the inlet end of the beam guiding cylinder is directed, in a direction transverse to the first direction.

2. The collimating device as claimed by claim 1, wherein the beam guiding cylinder adjusting device comprises a retractable adjusting rod configured to extend and retractably move in a transverse plane perpendicular to the first direction so as to adjust the direction towards which the inlet end of the beam guiding cylinder is directed.

3. The collimating device as claimed by claim 2, wherein the beam guiding cylinder adjusting device comprises four retractable adjusting rods configured to retractably move in four directions, i.e., upward, downward, leftward and rightward directions, in the transverse plane perpendicular to the first direction, so as to adjust the direction towards which the inlet end of the beam guiding cylinder is directed.

4. The collimating device as claimed by claim 2, wherein the beam guiding cylinder adjusting device further comprises a beam guiding cylinder adjusting screw configured to move the retractable adjusting rod in the direction transverse to the first direction by being screwed.

5. The collimating device as claimed by claim 1, wherein the beam guiding cylinder adjusting device further comprises a fixing plate configured to fix the inlet end of the beam guiding cylinder and extend in the plane transverse to the first direction.

6. The collimating device as claimed by claim 5, wherein the beam guiding cylinder adjusting device further comprises a flange plate coupled to the inlet end of the beam guiding cylinder, the flange plate including a portion extending along a plane where the fixing plate is located and a portion coupled to the inlet end of the beam guiding cylinder; and, a fastening screw that is mounted to the flange plate and contacts and presses the fixing plate by being screwed into a threaded hole in the flange plate so as to fix the direction towards which the inlet end of the beam guiding cylinder is directed.

7. The collimating device as claimed by claim 1, wherein the first collimator comprises a first collimation enhancing piece and the second collimator comprises a second collimation enhancing piece; and the first collimation enhancing piece and the second collimation enhancing piece extend along a central axis of the beam guiding cylinder and are sized such that most of scattering rays passing through the first collimator and/or the second collimator are blocked by the first collimation enhancing piece and the second collimation enhancing piece.

8. The collimating device as claimed by claim 7, wherein the first collimation enhancing piece and the second collimation enhancing piece are made of a material that can absorb rays, or, a side of the first collimation enhancing piece and the second collimation enhancing piece facing the central axis of the beam guiding cylinder is coated with the material that can absorb the rays so as to absorb scattering rays passing through the first collimator and/or the second collimator.

9. The collimating device as claimed by claim 7, wherein the first collimation enhancing piece and the second collimation enhancing piece each comprise a first portion coupled to the first collimator and/or the second collimator and a second portion extending parallel to the central axis of the beam guiding cylinder.

10. The collimating device as claimed by claim 7, wherein the first collimation enhancing piece and the second collimation enhancing piece each comprise a first baffle plate and a second baffle plate, and the first baffle plates and the second baffle plates are positioned symmetrically with respect to the central axis of the beam guiding cylinder, respectively.

11. The collimating device as claimed by claim 7, wherein the first collimation enhancing piece and the second collimation enhancing piece each are constituted by a baffle plate that is located at a side of the central axis of the beam guiding cylinder.

12. A ray inspection device comprising:
a frame;
a ray source configured to generate a ray;
an inspection region where an object to be inspected is placed or is passed;
a detecting device configured to detect a ray signal that has penetrated the object to be inspected; and
the collimating device as claimed by claim 1,
wherein the ray source, the inspection region, the detecting device and the collimating device are mounted to the frame.

13. The ray inspection device as claimed by claim 12, wherein the detecting device comprises a detector collimator configured to allow the ray that has penetrated the object to he inspected to enter the detector; and, the detector collimator is aligned with the second collimator of the collimating device and is fixed to the frame.

* * * * *